United States Patent [19]

Tremaine et al.

[11] Patent Number: Plant 5,695

[45] Date of Patent: Mar. 18, 1986

[54] CHRYSANTHEMUM PLANT NAMED STARGAZER

[76] Inventors: Harry G. Tremaine, 13755 N. Wells La., Lodi, Calif. 95240; Mary L. Hughes, 2320 Wagner Heights Rd., Stockton, Calif. 95209

[21] Appl. No.: 613,733

[22] Filed: May 24, 1984

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A chrysanthemum plant named Stargazer having flat capitulum form and daisy capitulum type, red-purple ray floret color, diameter across face of capitulum ranging from 5 to 6.5 cm. at maturity, uniform seven week photoperiodic flowering response to short days, short plant height when grown as a pinched, spray pot mum, spreading branching pattern, average natural season flowering date of September 20, and uniform response with durable color and form in Spring for small pot flowering programs.

3 Drawing Figures

The present invention comprises a new and distinct cultivar of *Chrysanthemum morifolium,* Ramat., named Stargazer.

Stargazer was discovered by Mary Lee Hughes on Aug. 20, 1979 while serving as an employee of Baileys Nursery, 5401 East Harney, Lodi, Calif. 95240 under the supervision of Harry G. Tremaine.

Stargazer was selected by Harry G. Tremaine as one flowered plant resulting from spontaneous mutation in a crop of the parent cultivar Stardom, disclosed by U.S. Plant Pat. No. 3,530.

The first act of asexual reproduction of Stargazer was accomplished by Harry G. Tremaine when vegetative cuttings were taken from the original selection in November, 1979 in a controlled environment in Lodi, Calif.

Horticultural examination of selected units initiated May 6, 1981 has demonstrated that the combination of characteristics as herein disclosed for Stargazer are firmly fixed and are retained through successive generations of asexual reproduction.

Stargazer has not been observed under all possible environmental conditions. The phenotype may vary significantly with variations in environment such as temperature, light intensity and day length. The observations, measurements and comparisons describe plants grown outdoors and under greenhouse conditions in Salinas, Calif. and Leamington, Ontario, Canada which approximate those generally used in commercial practice.

For outdoor culture rooted cuttings were established in soil in one gallon containers, and thereafter maintained outdoors under the natural temperature and day length prevailing during July through September. Single pinching was practiced with all branches, and buds retained.

The following traits have been repeatedly observed and are determined to be basic characteristics of Stargazer which in combination distinguish this chrysanthemum as a new and distinct cultivar:

(1) Flat capitulum form.

(2) Daisy capitulum type.

(3) Red-purple ray floret color.

(4) Diameter across face of capitulum ranging from 5 to 6.5 cm. at maturity.

(5) Uniform seven week photoperiodic flowering response to short days.

(6) Short plant height (requiring 2 long day weeks prior to pinch followed by 3 to 7 long days prior to short days, and 0 to 1 application of 2500 ppm B-9 SP in 7 to 14 days after the beginning of short days to attain a flowered plant height of 25 to 35 cm. in 6" pots).

(7) Spreading branching pattern.

(8) Average natural season flowering date of September 20.

(9) Uniform response with durable color and form in Spring for small pot flowering programs.

The accompanying photographic drawings depict typical leaf and inflorescence characteristics of Stargazer. Sheet 1 is a color photograph of a plant of Stargazer grown as a pinched spray pot mum, with colors being as accurate as possible with renditions of this type. Sheet 2 is a black and white photograph of three views of the inflorescence of Stargazer. Sheet 3 shows the leaves of Stargazer in three stages of development (mature, intermediate and immature).

Of the many commercial cultivars known to the present inventors, the most similar in comparison to Stargazer is Stardom, U.S. Plant Pat. No. 3,530. Reference is made to attached Chart A which compares certain characteristics of Stargazer to those same characteristics of Stardom.

Stargazer develops a significantly deeper ray floret color. It displays 71 A,B (R.H.S. Colour Chart) vs. 65 A, B for Stardom in an outdoor environment in September in Salinas, Calif. The ray floret count of Stardom is approximately 42% higher, with Stargazer being more a daisy type. Branching pattern, height, response and natural flowering dates are similar.

In the following description, color references are made to The Royal Horticultural Society Colour Chart. The color values were determined between 11:00 and 11:30 A.M. on May 12, 1983 and again Dec. 6, 1983 at 9:00 A.M. under 150 foot-candle light intensity at Salinas, Calif.

Classification:

*Botanical.—Chrysanthemum morifolium.* — Ramat., cv Stargazer.

*Commercial.*—Daisy spray pot and garden mum.

I. Inflorescence:

A. *Capitulum.*—Form: Flat. Type: Daisy. Diameter Across Face: 5 to 6.5 cm.

B. *Corolla of ray florets.*—Color (General Tonality From a Distance of Three Meters): Red-purple. Color (abaxial): 71A, B oxidizing to 74B,C. Color (adaxial): 75A, B. Shape: Variable with temperature. Both flat keeled from tip to base and spoon formed notched tip.

C. *Corolla of disc florets.*—Color (mature): 13A. Color (immature): 154A developing rapidly to 1A.

D. *Reproductive organs.*—Androecium: Present disc florets only; moderate pollen. Gynoecium: Present both ray and disc florets.

II Plant:

A. *General appearance.*—Height: Short. Branching Pattern: Spreading.

B. *Foliage.*—Color (abaxial): 137A. Color (adaxial): 137C. Shape: Moderately lobed. Moderately serrated.

CHART A

COMPARISON OF STARGAZER AND STARDOM

| CULTIVAR | RAY FLORET COLOR | CAPITULUM FORM AND TYPE | BRANCHING PATTERN |
|---|---|---|---|
| STARGAZER | RED-PURPLE | WINTER/SPRING AVG. 75 RAY FLORETS FLAT DAISY SUMMER/FALL - AVG. 200 RAYS | SPREADING |
| STARDOM | GREYED LAVENDER | WINTER/SPRING - AVG. 145 RAY FLORETS FLAT DUPLEX SUMMER/FALL - AVG. 320 RAYS | SPREADING |

CHART A-continued

COMPARISON OF STARGAZER AND STARDOM

| CULTIVAR | DIAMETER ACROSS FACE OF CAPITULUM | PLANT HEIGHT | FLOWERING RESPONSE PERIOD | PERMANENCE |
|---|---|---|---|---|
| STARGAZER | 5.0 to 6.5 cm. | SHORT 22 to 30 cm. | 7 WEEKS | 14-21 DAYS |
| STARDOM | 5.5 to 7.0 cm. | SHORT 22 to 30 cm. | 7 WEEKS | 14-21 DAYS |

COMPARISONS MADE OF PLANTS GROWN AS OUTDOOR PINCHED SPRAY POT MUMS IN SALINAS, CALIFORNIA AND LEAMINGTON, ONTARIO, CANADA.

We claim:

1. A new and distinct cultivar of *Chrysanthemum morifolium,* Ramat., plant named Stargazer, as described and illustrated, and particularly characterized as to uniqueness by the combined characteristics of flat capitulum form; daisy capitulum type; red-purple ray floret color; diameter across face of capitulum ranging from 5 to 6.5 cm. at maturity, uniform seven week flowering response; short plant height; spreading branching pattern; average natural season flowering date of September 20, and uniform response with durable color and form in Spring for small pot flowering programs.

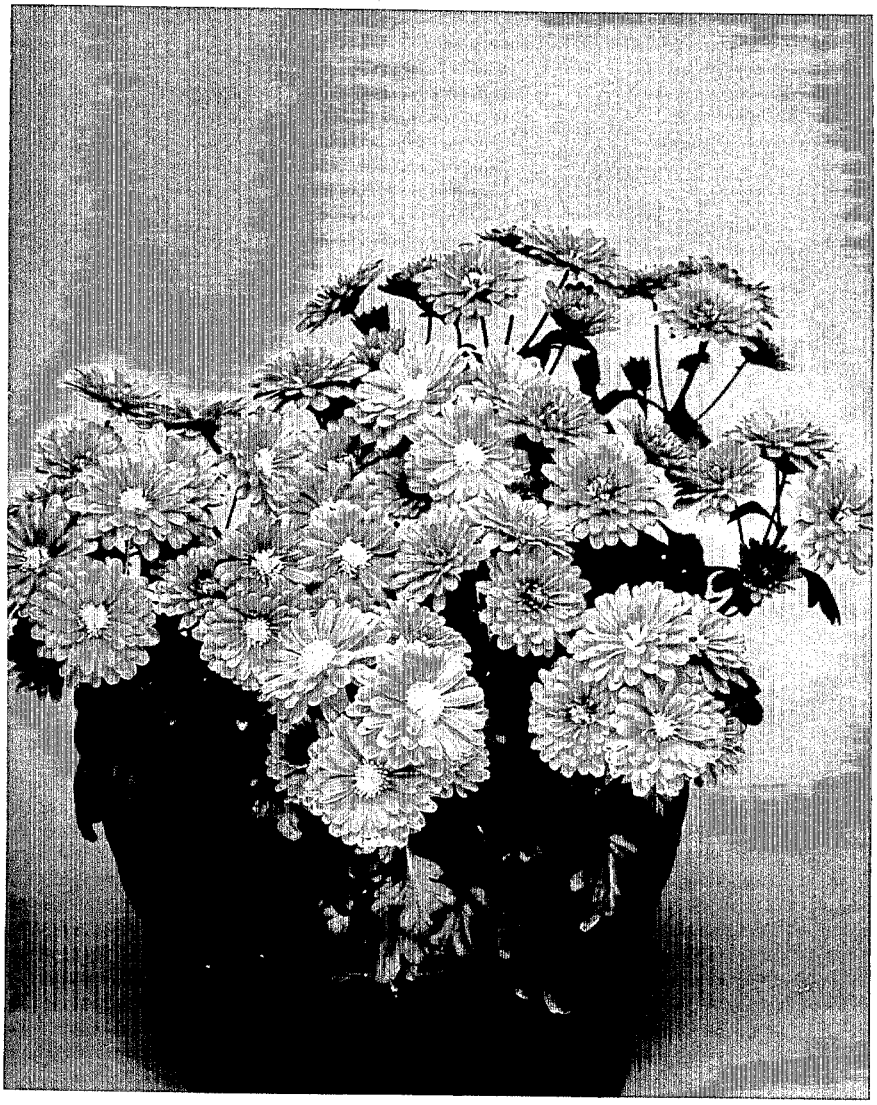

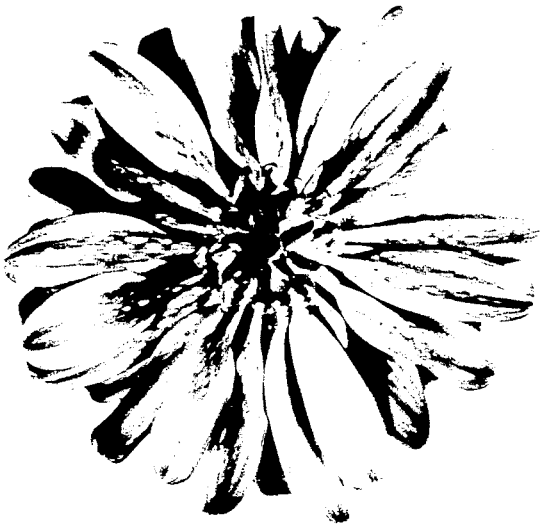
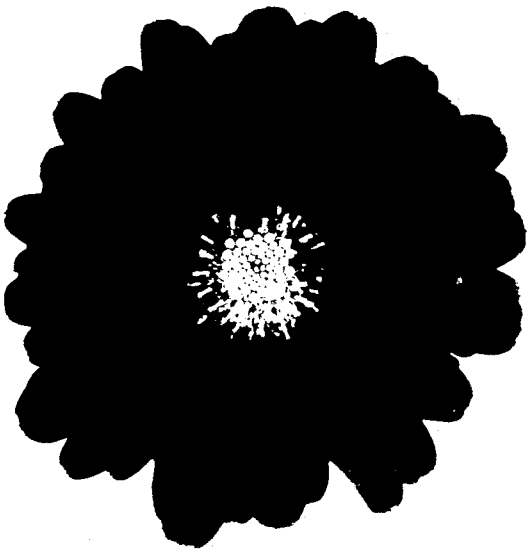
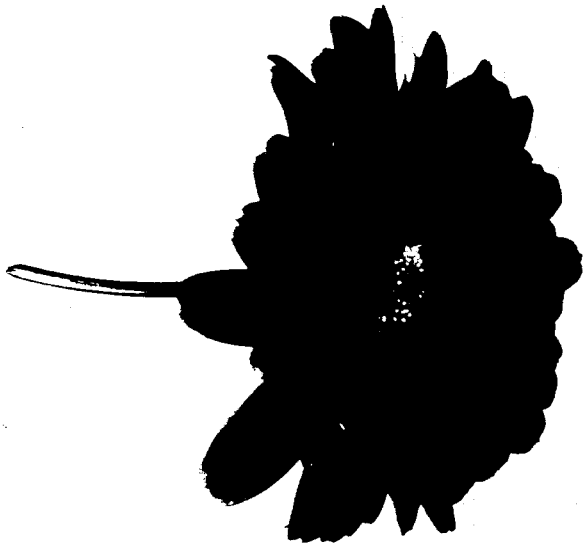

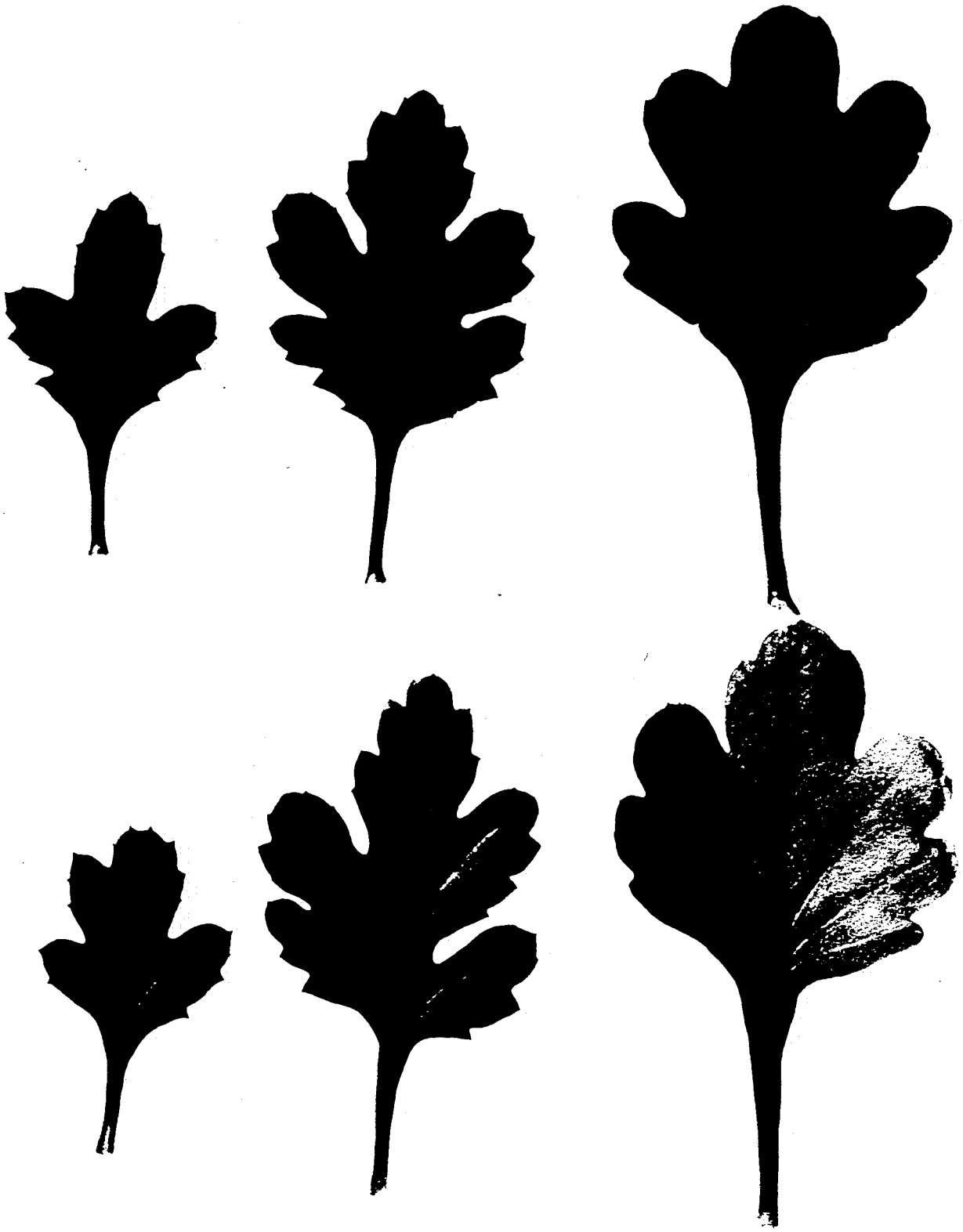

* * * * *